United States Patent
Chen et al.

(10) Patent No.: US 8,321,055 B2
(45) Date of Patent: Nov. 27, 2012

(54) SYSTEM AND METHOD FOR MULTIPLE VIEW MACHINE VISION TARGET LOCATION

(75) Inventors: Mo Chen, Liverpool, NY (US); Robert Mumford Gowans, Mexico, NY (US)

(73) Assignee: JADAK, LLC, North Syracuse, NY (US)

( * ) Notice: Subject to any disclaimer, the term of this patent is extended or adjusted under 35 U.S.C. 154(b) by 412 days.

(21) Appl. No.: 12/611,783

(22) Filed: Nov. 3, 2009

(65) Prior Publication Data

US 2011/0106312 A1    May 5, 2011

(51) Int. Cl.
G05B 15/00    (2006.01)
G05B 19/00    (2006.01)
G05B 11/01    (2006.01)

(52) U.S. Cl. .................. 700/259; 700/1; 700/2; 700/28; 700/29; 700/32; 700/245; 700/246; 700/250; 700/254

(58) Field of Classification Search .................. 700/1, 2, 700/7–9, 28, 29, 32, 245, 246, 250, 253, 700/254, 73, 259; 250/559.29; 345/158; 356/4.07, 479, 497, 614, 620; 382/153, 154; 901/47
See application file for complete search history.

(56) References Cited

U.S. PATENT DOCUMENTS

| | | | | |
|---|---|---|---|---|
| 4,575,304 A * | 3/1986 | Nakagawa et al. | ........... | 414/730 |
| 4,754,415 A * | 6/1988 | George et al. | .................. | 700/250 |
| 5,374,830 A * | 12/1994 | Pryor | ........................ | 250/559.3 |
| 5,940,178 A * | 8/1999 | Barber et al. | .................. | 356/339 |
| 5,985,215 A * | 11/1999 | Sakazume et al. | ............. | 422/67 |
| 6,060,022 A * | 5/2000 | Pang et al. | ...................... | 422/65 |
| 6,190,617 B1 * | 2/2001 | Clark et al. | .................... | 422/562 |
| 6,599,476 B1 * | 7/2003 | Watson et al. | .................. | 422/63 |
| 7,216,042 B2 * | 5/2007 | Okamura et al. | ............... | 702/31 |
| 7,291,309 B2 * | 11/2007 | Watson et al. | .................. | 422/63 |
| 7,447,615 B2 * | 11/2008 | Watanabe et al. | ................ | 703/7 |
| 7,481,978 B2 * | 1/2009 | Li et al. | ......................... | 422/561 |
| 7,610,115 B2 * | 10/2009 | Rob et al. | ...................... | 700/245 |
| 2003/0164934 A1 * | 9/2003 | Nishi et al. | ..................... | 355/72 |
| 2004/0097790 A1 * | 5/2004 | Farkas et al. | ................. | 600/160 |
| 2006/0257999 A1 * | 11/2006 | Chang et al. | .............. | 435/289.1 |
| 2007/0065947 A1 * | 3/2007 | Dong et al. | ..................... | 436/80 |
| 2007/0112465 A1 * | 5/2007 | Sadighi et al. | ............... | 700/254 |
| 2007/0134131 A1 * | 6/2007 | Watson et al. | .................. | 422/65 |
| 2007/0159615 A1 * | 7/2007 | Horiuchi | ......................... | 355/72 |
| 2008/0106387 A1 * | 5/2008 | Miller | ......................... | 340/10.5 |
| 2008/0151263 A1 * | 6/2008 | Randers-Pehrson et al. | . | 356/601 |
| 2008/0228404 A1 * | 9/2008 | Garty et al. | ..................... | 702/19 |
| 2008/0273758 A1 * | 11/2008 | Fuchs et al. | ................... | 382/106 |
| 2009/0042281 A1 * | 2/2009 | Chang et al. | .............. | 435/287.2 |
| 2009/0054222 A1 * | 2/2009 | Zhang et al. | .................... | 494/17 |

* cited by examiner

*Primary Examiner* — Ian Jen (74) *Attorney, Agent, or Firm* — David L. Nocilly; Bond Schoeneck & King (57) ABSTRACT

A machine vision system for controlling the alignment of an arm in a robotic handling system. The machine vision system includes an optical imager aligned to simultaneously capture an image that contains a view of the side of an object, such as a test tube, along with a view of the top of the object provided by a mirror appropriately positioned on the robotic arm. The machine vision system further includes a microcontroller or similar device for interpreting both portions of the image. For example, the microcontroller may be programmed to determine the location of the object in the reflected portion of the image and transpose that information into the location of the object relative to the robotic arm. The microcontroller may also be programmed to decode information positioned on the object by interpreting visual information contained in the other portion of the captured image.

18 Claims, 11 Drawing Sheets

SYSTEM AND METHOD FOR MULTIPLE VIEW MACHINE VISION TARGET LOCATION

BACKGROUND OF THE INVENTION

1. Field of the Invention

The present invention relates to machine visions systems and, more specifically, to a system and method for target location in robotic handling systems.

2. Description of the Related Art

Machine vision plays an important role in automated and robotic systems, such as assembly line manufacturing, quality control inspection, and sample processing. Conventional systems are generally comprised of an optical imager, such as a charged coupled device (CCD) or similar device using digital imaging technology, which is positioned to capture images of objects that pass in front of it. In low-light or enclosed applications, machine vision systems may include an illumination source, such as a bank of light emitting diodes (LEDs), positioned proximately to the imager. The images are subsequently processed to decode information contained in the resulting two-dimensional image, such as 1D linear codes, 2D stacked/matrix codes, OCR fonts, and postal codes. The image captured by the machine vision system may also be subjected to more advanced processing, such as shape recognition or detection algorithms, that provide information about the object of interest in the image.

In robotic sample handling systems, such as blood analyzers and the like, samples are moved to and from diagnostic modules for automatic testing and retesting using a loading rack that holds a plurality of carriers, such as test tubes filled with samples. Proper location of the test tubes is often critical for navigation and control so that the robotic systems can more easily and accurate position tubes.

BRIEF SUMMARY OF THE INVENTION

It is therefore a principal object and advantage of the present invention to provide a system and method for identifying the location of a target in a robotic handling system.

It is another object and advantage of the present invention to provide a system and method for improving robotic arm calibration in robotic handling system.

It is a further object and advantage of the present invention to provide a system and method for easily locating targets in a robotic handling system and identifying information encoded or placed on a target.

It is an additional object and advantage of the present invention to provide a system and method for more quickly locating targets in a robotic handling system and identifying information encoded or placed on a target.

In accordance with the foregoing objects and advantages, the present invention provides a system for locating objects, such as test tubes, in loading rack, guiding robotic handling and obtaining information about the objects. The system comprises an optical imager positioned relative to a standard robotic arm. The imager may be fixed relative to the arm, such as on a part of the arm assembly, or fixed in a given location in the larger robotic system. The imager is configured to simultaneously obtain images of the side and top of an object, and measure the difference between the center of the object and the center of the arm to assist with alignment of the arm with the object. Upon a successful grasping of the object, the images captured by imager may be used to interpret data placed on the object, such as by decoding a barcode.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1A:
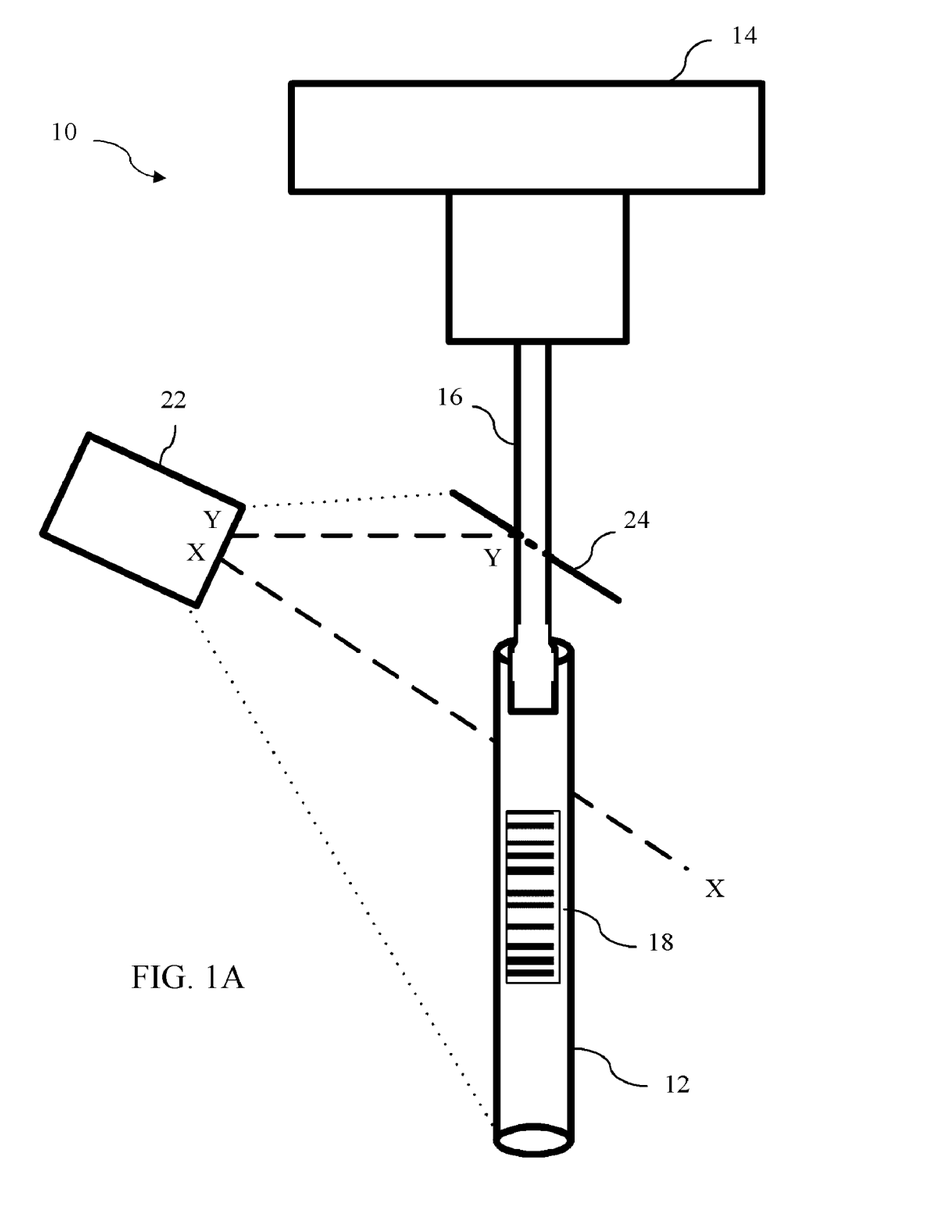
FIG. 1A is a side view of multiple view vision system according to the present invention.
Figure 1B:
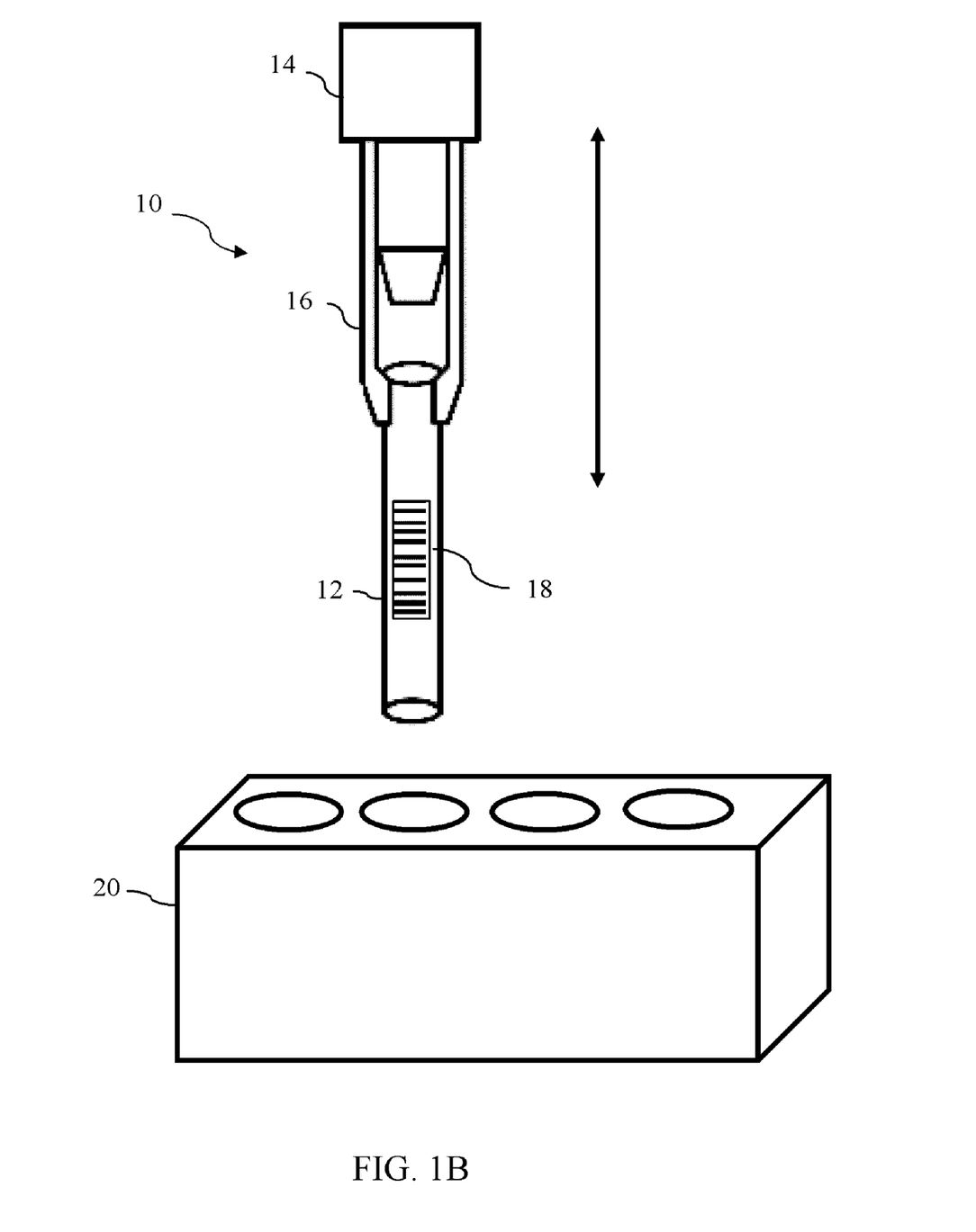
FIG. 1B is a front view of multiple view vision system according to the present invention.

Referring now to the drawings, wherein like reference numerals refer to like parts throughout, there is seen in FIGS. 1A and 1B a machine vision system 10 for locating a target, such as test tube 12, in a robotic handling system 14. In general, robotic handling systems are motorized systems that move and transfer patient sample tubes between designated locations, such as from one rack to another rack. A patient sample tube frequently contains different body fluids (such as blood, urine, etc.) and can comprise any variety of test tube. For example, tubes 12 may need to be transferred from a storage tray to a test tray 20, and then back to the storage tray, by a robotic arm 16. Arm 16 is typically moved into a location approximately three to four inches above tube 12 prior to moving down to grip tube 12. Quite often, arm 16 is not in acceptable alignment with tube 12, such as when tube 12 is improperly positioned in tray 20, tray 20 is not well positioned, or arm 16 has become be misaligned. As a result, arm 16 is unable to successfully grasp tube 12 and may even damage tube 12 in the process.

Tubes 12 may further include a barcode 18 or other indicia thereon. Those of skill in the art will recognize that there are numerous ways to encode information on a target, and the term "barcode" is used herein to generally describe information placed on a target, whether in an encoded or special format, such as a 2D barcode, or in another format, such as text or handwriting. Machine vision system 10 is configured to provide planar translation shift information between the center of the robotic arm 16 and the center of a tube 12, which assists the robotic arm 16 in grasping and removing tube 12. When a tube 12 is moved by arm 16, system 10 may also be used to decode barcode 18 or capture and interpret any other indicia on the tube.

As further seen in FIGS. 1A and 1B, system 10 includes an optical imager 22 positioned relative to robotic arm 16. Imager 22 may be fixed relative to arm 16, such as on a part of the assembly that comprises arm 16, or fixed in a given location in system 10. Imager 22 is configured to measure the difference between the center of tube 12 and the center of arm 16 to assist with alignment of arm 12 and tube 16. Arm 16 may then be realigned with tube 16 for successful grasping and removal from tray 20. Upon a successful removal of tube 16, imager 22 may be used to interpret data placed on tube 16, such as by decoding a barcode 18.

Figure 2:
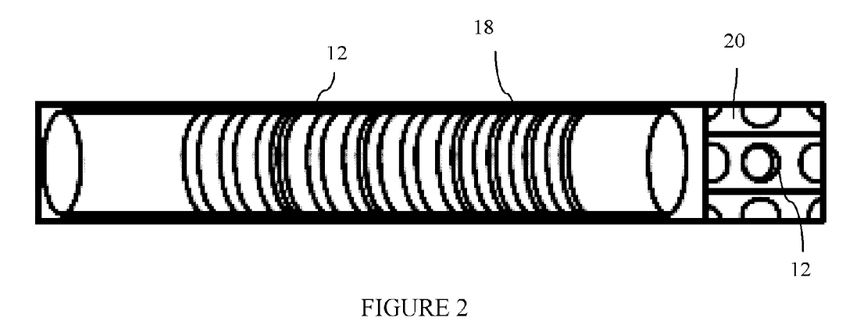
FIG. 2 is a schematic of an image captured by a multiple view vision system according to the present invention.

System 10 further includes a mirror 24 positioned within arm 16 and aligned to fall within a portion of the field of view of imager 22. Mirror 24 allows allow imager 22 to capture an image of the top of tube 16. As further seen in FIGS. 1A, imager 22 is aligned along an axis X-X that is offset from the reflected ray axis Y-Y of mirror 24. As seen in FIG. 2, the field of view by imager 22 includes both mirror 24 positioned above tube 12 and tube 12 itself, thus any images captured by imager 22 with include a reflected image of the top of tube 12 in the upper portion of the image and the body of tube 12, including any barcode 18 or indicia placed therein, in the lower portion of the image. It should be recognized by those of skill in the art that mirror 24 may be replaced with another item that reflects the appropriate information to imager 22 or omitted entirely if imager 22 is positioned in a way that all of the necessarily fields of view may be captured at the same time.

Figure 3:
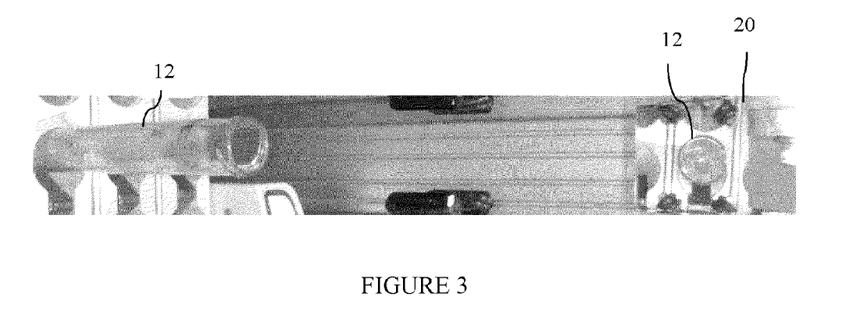
FIG. 3 is an actual image captured by a multiple view vision system according to the present invention.

Referring to FIG. 3, a sample image captured by imager 22 of tube 12 may be adjusted by reducing the configuration settings of imager 22 to only encompass the desired areas, thereby improving processing time. As a result of the use of minor 24, the side view and top view of tube 12 are positioned on the left side and the right side of the image, respectively. The configuration of system 10 provides imager 22 with a broader field of views and therefore allows the use of a single imager 22 to perform both tube location and barcode detection and decoding. The use of a single imager also allows for the use of identical system parameters, so that there is only one digital channel transferring the acquired image and imager parameters, such as bandwidth characteristics, and distortion, are identical. In addition, there is only one set of camera and vision parameters needed. Furthermore, the design of system 10 allows for simpler, and thus cheaper, construction and improves visions processing time.

Figure 4:
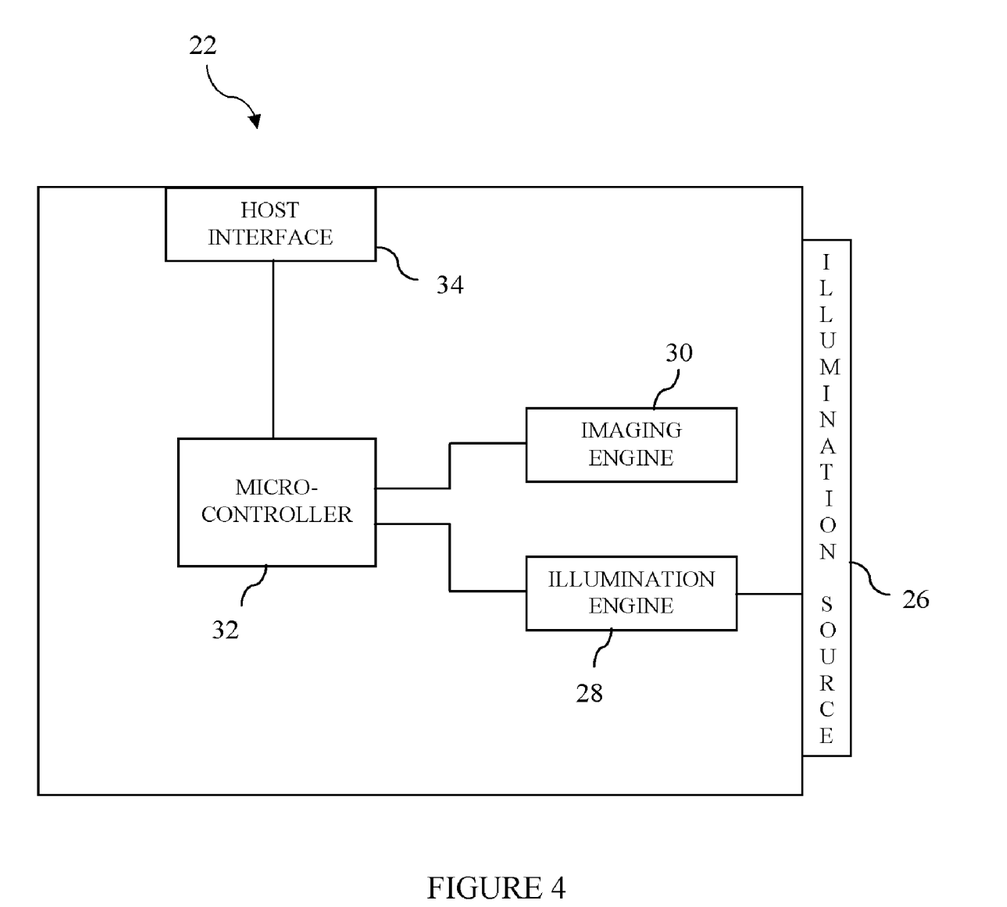
FIG. 4 is a high-level schematic of an imager according to the present invention

Referring to FIG. 4, imager 22 may comprise any various off-the-shelf optical imagers. For example, Hand Held Products, Inc. of Skaneateles Falls, N.Y. Sells 5080 and 5180 series imagers that are capable of scanning and decoding most standard barcodes including linear, stacked linear, matrix, OCR, and postal codes. Other optical imaging platforms may include the EV12, EV15, EA15, and XA21 imagers available from Intermec Technologies Corporation of Everett, Wash., or any custom imaging packaging sold commercially for incorporation into machine vision or optical imaging systems. Preferably, imager 22 comprises an illumination source 26, such as an LED direct front flash light, an associated illumination engine 28, imaging engine and accompanying digital camera engine and optics 30, and a digital signal processing processor 32 (96 MHz MXL fixed-point processor). Illumination source 26 of imager 22 provides diffuse light for system 10. Although vision processing may be performed on the onboard digital signal processor, those of skill in the art will recognize that a separate microcontroller may be employed in combination with imager 22 to perform any necessary vision processing or calculations.

Preferably, imager 22 is programmed to report the decoded barcode data, liquid level and stitched panoramic tube image in a compressed form (such as JPEG) to a host device through host interface 34 using a conventional protocol, such TCP/IP, through an Ethernet connection, so that system 10 proceeds to present the next tube 12 of interest to imager 22. Interface 34 may also comprise a conventional RS232 transceiver and associated 12 pin RJ style jack or other conventional buses, such as USB, IEEE 1394, 12C, SPI, or PCMCIA, or other connector styles, such as an FFC style.

Imager 22 is preferably connected to a host system through either RS232 serial port or TCP/IP protocol and configured as a slave device to accept control and configuration commands from and returning the information to the host system. In particular, system 10 will report the 2-D translation planar shift vector from the center of tube 12 to the center of robotic arm 16 as well as decoded barcode data to the host.

Figure 5:
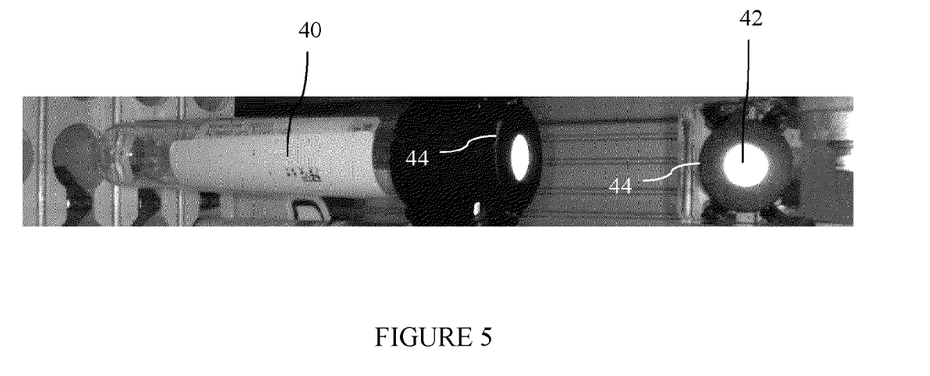
FIG. 5 is a multiple view image of a test tube according to the present invention.

Vision calibration is performed offline in order to prepare some information for the on-line vision operations. The calibration information depends only on the fixture setup, as seen in FIG. 1, and does not change unless the fixture is altered. The calibration information first includes the barcode window and tube center window location. As seen in FIG. 5, the resulting image captured by imager 22 is constructed in such a way that, for example only, the view of the tube side is mapped directed on the left side of the image whereas the view of the tube top is reflected through the mirror and mapped on the right side of the resulting image. Although these view are presented side by side in the captured image, the barcode reading and the tube center alignment processing may be performed independently from each other. In the other words, barcode decoding is still preferably performed within the barcode window of the image (left side), while the tube center alignment processing is executed in the tube center window of the image (right side).

Calibration information also includes the center of the robotic arm 16. In order to align arm 16 to the center of tube 12, the position of the center of tube 12 must be determined. Because the relative position between imager 22, mirror 24 and arm 16 is fixed, the center of arm 16 relative to the center of tube 12 in the appropriate region of interest should be held constant from image to image.

The last calibration information needed is the appropriate conversion between the pixels of a captured image to the corresponding length measurement in the physical elements of system 10, such as millimeters. System 10 locates the center of tube 12 and obtain the translation vector between the center of arm 16 and the center of tube 12 in image pixels. However, most robotic systems move arms 16 in units such as millimeters or inches. Accordingly, a scalar value must be used to translate the image plan in pixels to the appropriate world coordinates.

Figure 6:
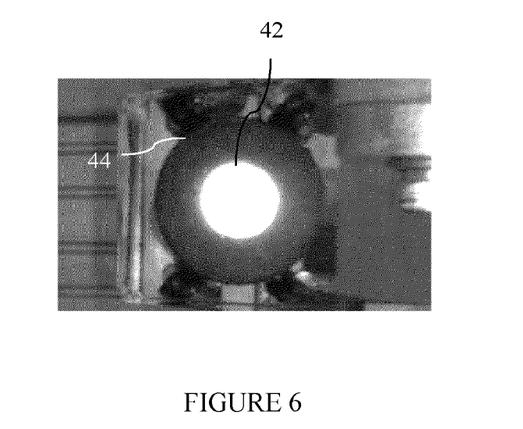
FIG. 6 is a portion of a multiple view image of a test tube according to the present invention.

Vision calibration in system 10 is a two-step process by using a special calibration tube 40. As seen in FIGS. 5 and 6, a preferred calibration tube 40 is a standard size tube having a circle 42 formed from retro-reflective material glued in the cap 44 of tube 40. The center of the retro-reflective circle 42 coincides with the center of calibration tube 40, and the diameter of circle 42 should be equal to the maximum tube center shift possible from the center of arm 16.

Figure 7:
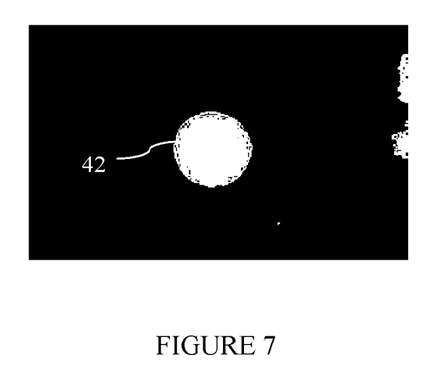
FIG. 7 is a portion of a multiple view image of a test tube that has been processed according to the present invention.

A simple two-step calibration process may be used to perform the following tasks to gather the appropriate calibration information. First, arm 16 holds calibration tube 40 and imager 22 captures an image, as seen in FIG. 5. Due to its special characteristics, the retro-reflective circle 42 reflects all the camera LED flash light back to the camera, which results in a fully saturated circular object in the image. Using the right one-third of the image seen in FIG. 5 (*b*), it is thresholded to form a binary image, as seen in FIG. 7. Since the retro-reflective material will create a fully saturated region, i.e., a pixel value of 255, the thresholding should be very simple and easy. For example, setting the threshold to be 250 should be acceptable. A connected component labeling technique is then applied to the threshold image to label each different isolated object.

Figure 8:
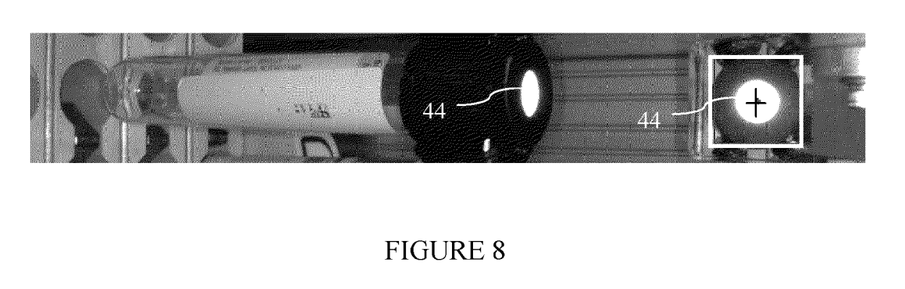
FIG. 8 is a multiple view image of a test tube according to the present invention.

The region properties of the labeled object, such as size, circularity, centroids, and the bounding box, may then be extracted, as seen in FIG. 8. The retro-reflective circle 42 is located by finding the circular and largest connected object. Since arm 16 holds the tube in this step, its center coincides with the center of the cap of tube 12, which is also the center of retro-reflective circle 42. The center of arm 16 ($x_g$, $y_g$) may then be determined by computing the planar 2D center of retro-reflective circle 42, identified with a black cross (+) in FIG. 8. Because the diameter of retro-reflective circle 42 may be set to equate to the maximum tube center shift $W_s$ from the center of arm 16, the region of interest window, i.e., the white square in FIG. 8, can be determined to be the square whose center is ($x_g$, $y_g$) and width is the two times of the detected diameter of the retro-reflective circular object, i.e., $2W_s$. The barcode region of interest is the remaining portion of the image left of the left boundary of the tube center window.

Figure 9:
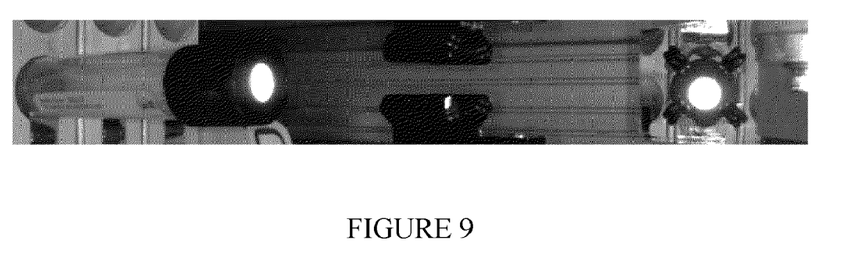
FIG. 9 is a multiple view image of a test tube according to the present invention.
Figure 10:
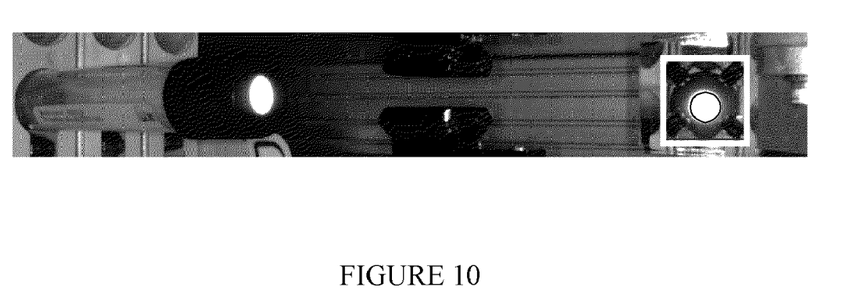
FIG. 10 is a multiple view image of a test tube according to the present invention.

The next step to acquire a scale value to convert the distance from the pixels in the image to the millimeters in the real world. An image, such as FIG. 9, is captured when tube 16 is placed inside rack 22 and arm 16 is positioned directly above. The tube center region of interest in a captured imaged is thresholded, segments are labeled by performing connect component labeling, the properties of the regions, as seen in FIG. 10, are computed using the labeled components. The conversion scale $f_c$ is computed by dividing the diameter of the located saturated circle measured in pixels by the diameter of this circle measured in millimeter using caliber in priori.

The location of round objects is important in many areas of image analysis, but it is especially important in industrial applications such as automatic inspection and assembly. Among all the existing circle detection techniques, Hough Transform (HT) is perhaps the most straightforward and reliable technique for the project under investigation since HT has been found to be particularly good at dealing with all sorts of difficulties. In the HT method for finding circles, the intensity gradient is first estimated at all locations in the image and is then threshold to give the positions of the significant edges. Then the positions of all possible center locations—namely, all points a distance R away from every edge pixel are accumulated in parametric space, with R being the anticipated circle radius. The number of points accumulated is equal to the number of edge pixels in the image. Parametric space can be a general storage area, but when looking for circles it is convenient to make it congruent to image space; in that case, possible circles centers are accumulated in a new place of image space. Finally, parameter space is searched for peaks that correspond to the centers of circular objects. The equation of the curve can be given in explicit form like Equation (1) below.

$$(x-x_0)^2 (y-y_0)^2 = r^2 \quad \text{,Equation (1)}$$

This equation defines a locus of points (x, y) centered on an origin ($x_0$, $y_0$) and with radius r. This equation can be visualized in two ways: as a locus of points (x, y) in an image, or as a locus of points ($x_0$, $y_0$) centered on (x, y) with radius r.

Figure 11:
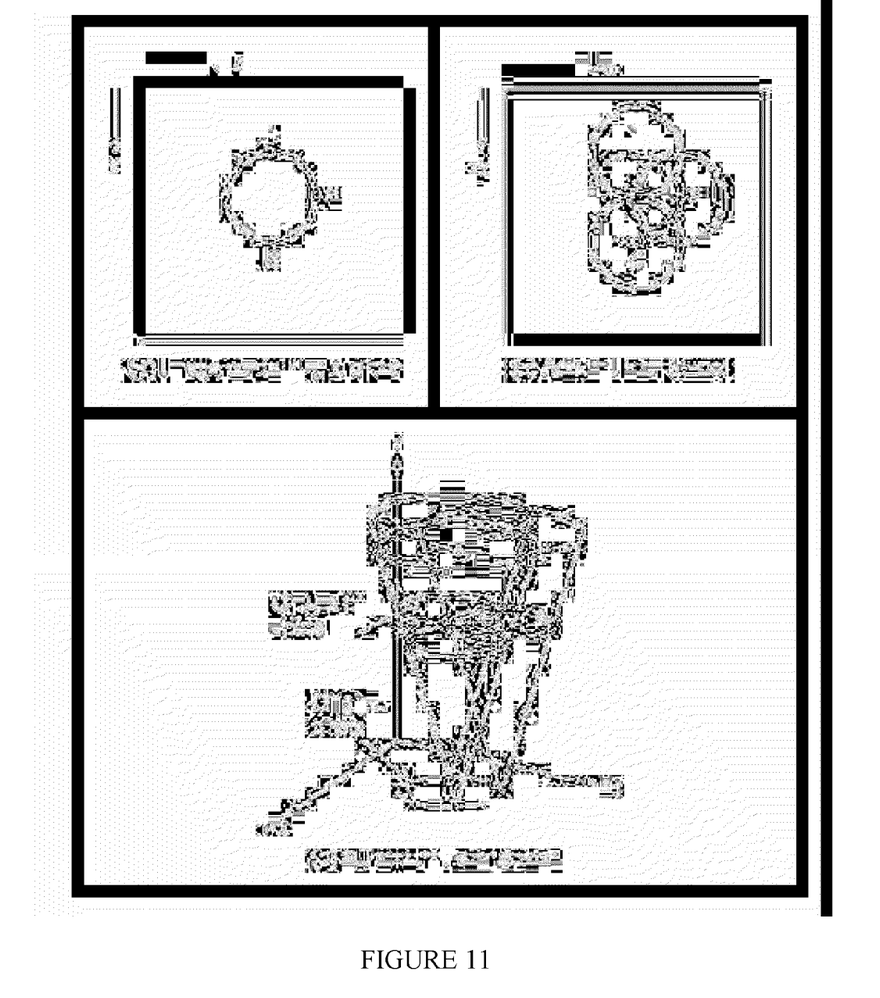
FIG. 11 is a series of schematics of an image processing procedure according to the present invention.

FIG. 11 illustrates this dual definition. Each edge point in FIG. 11(*a*) defines a set of circles in the accumulator space. These circles are defined by all possible values of the radius and they are centered on the coordinates of the edge point. FIG. 11(*b*) shows three circle defined by three edge points. These circle are defined for a given radius value. Each edge point defines circles for the other value of the radius. This implies that the accumulator space is three dimensional (for the three parameters of interest) and that edge points map to a cope of votes in the accumulator space. FIG. 11(*c*) illustrates this accumulator. Every edge point will be mapped to all possible points in the accumulator space. After gathering evidence of all the edge points, the maximum peak in the accumulator space corresponds to the parameters of the circle in the original image.

For detection of a circle, as shown in Equation (1), the accumulator space parameters are ($x_0$, $y_0$, r). Circle detection requires examination of a three-dimensional parameter space. This three dimension is the cause of excessive computational and memory expense, and it is for this reason that the circle Hough transforms are less popular and non-practical in the real time machine vision application. There, although circle Hough transform is quiet appealing, the involved costs may contradicts with the requirements for system 10. Accordingly, the regular circle Hough transforms may be simplified by taking advantage of system 10 with some loss of the location accuracy, provided that arm 16 allows some tolerance when lifting tube 12 without any problems.

Figure 12:
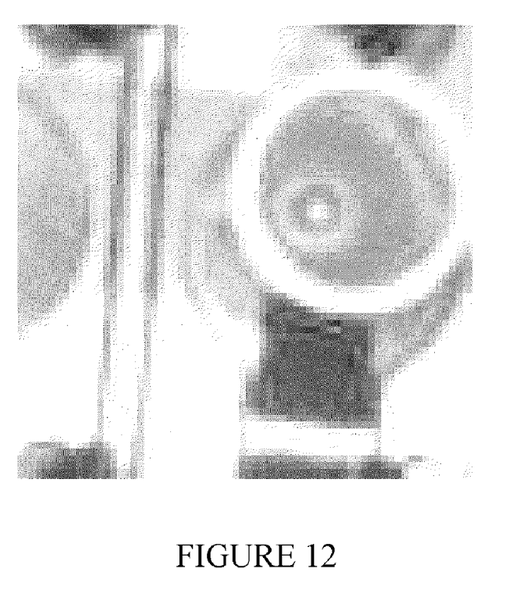
FIG. 12 is a portion of a multiple view image of a test tube according to the present invention.

To simplify processing, the captured image is downsampled by M, as seen in FIGS. 12, where M=2. Next, simple edge detection is used to extract the vertical edges as follows:

$$g_{M\downarrow}(x,y) = \begin{cases} 1, & |I_{M\downarrow}(x, y-1) - I_{M\downarrow}(x, y+1)| > T \\ 0, & |I_{M\downarrow}(x, y-1) - I_{M\downarrow}(x, y+1)| < T \end{cases} \quad \text{Equation (2)}$$

where g(x, y) is the extracted edge image, I(x, y) represent the gray intensity of the image, and T is the edge threshold (T is chosen to be 0.04-0.08 of the maximum intensity I(x, y) in the image(, respectively. In Equation (2), the edge is invariant to 180 degree, which treats the edge points from the back to white and from the white to back same. Since no edge thinning is perform, Equation (2) results in a thicker edge, but this thicker edge is generated on purpose to give the redundancy which will be needed in the following simplification. Moreover, because the maximum tube center misalignment between the tube center and gripper center is $W_s$, the unnecessary edge points can be further eliminated by setting all the edge point which is out of the possible tube center zero by using the following formula because the edge points are just clutter:

$$g_{M\downarrow}(x,y) = 0, \sqrt{(x-x_g)^2 + (y-y_g)^2} > W_s/M$$

Figure 13:
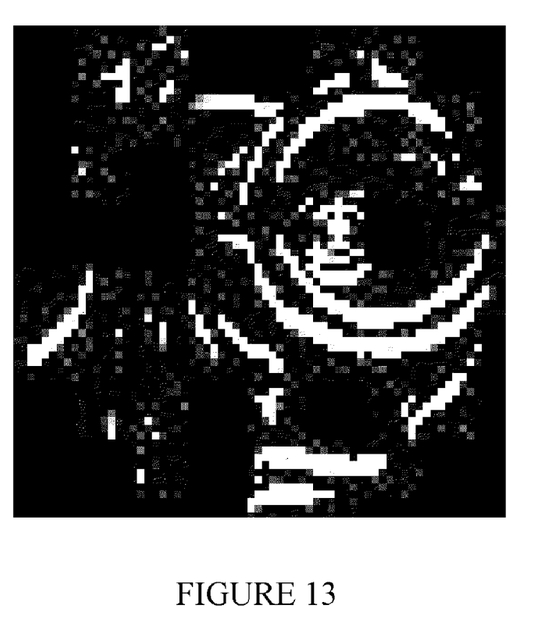
FIG. 13 is a portion of a multiple view image of a test tube that has been processed according to the present invention.

The edge detection results are shown in FIG. 13.

According to the conventional tube manufacturing standards, the diameters of a sample tube could be either 12 mm or 15 mm. Hence, the radius search may be limited by $$\left\lfloor \frac{12 f_c}{M} \right\rfloor - \tau \leq r \leq \left\lceil \frac{12 f_c}{M} \right\rceil + \tau, \left\lfloor \frac{15 f_c}{M} \right\rfloor - \tau \leq r \leq \left\lceil \frac{15 f_c}{M} \right\rceil + \tau,$$

where $\lfloor x \rfloor$ and $\lceil x \rceil$ represent the nearest integer smaller and greater x, respectively, and τ is a search margin (τ) is between 1-4 pixels). As there is only one tube in the field of view, the center of tube 12 may be located by finding the maximum instead of finding the highest peak in the image. Although not described in detail herein, some of the circle Hough transform accumulator space decomposition could be applied to further reduce the circle Hough transform complexity by using the pairs of the edge points.

Figure 14:
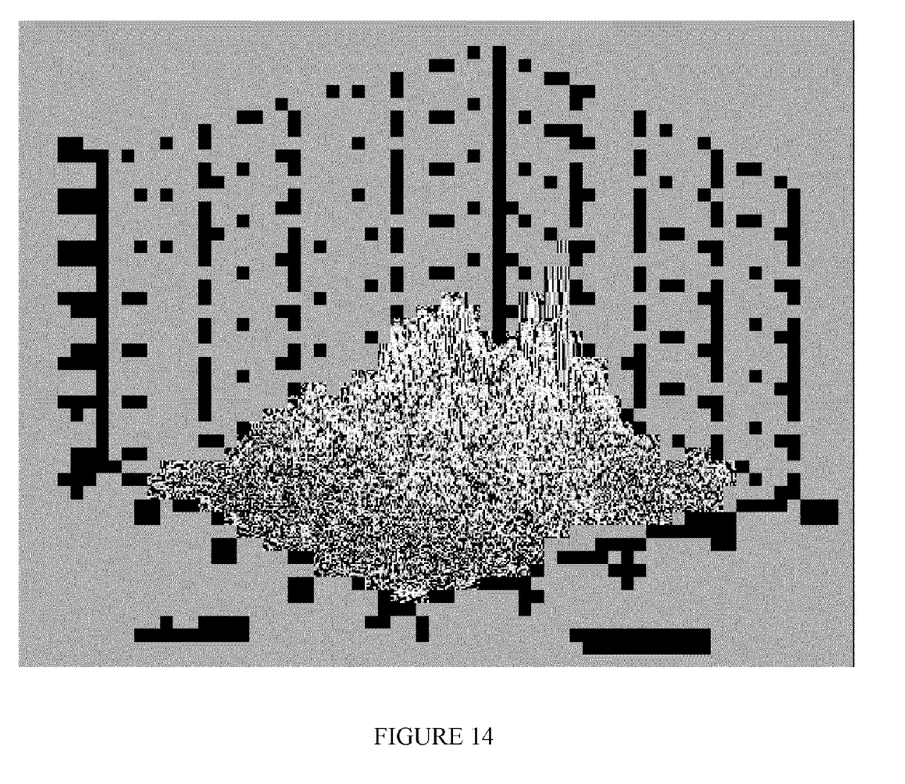
FIG. 14 is a graph of a Hough transform accumulator space decomposition according to the present invention.
Figure 15:
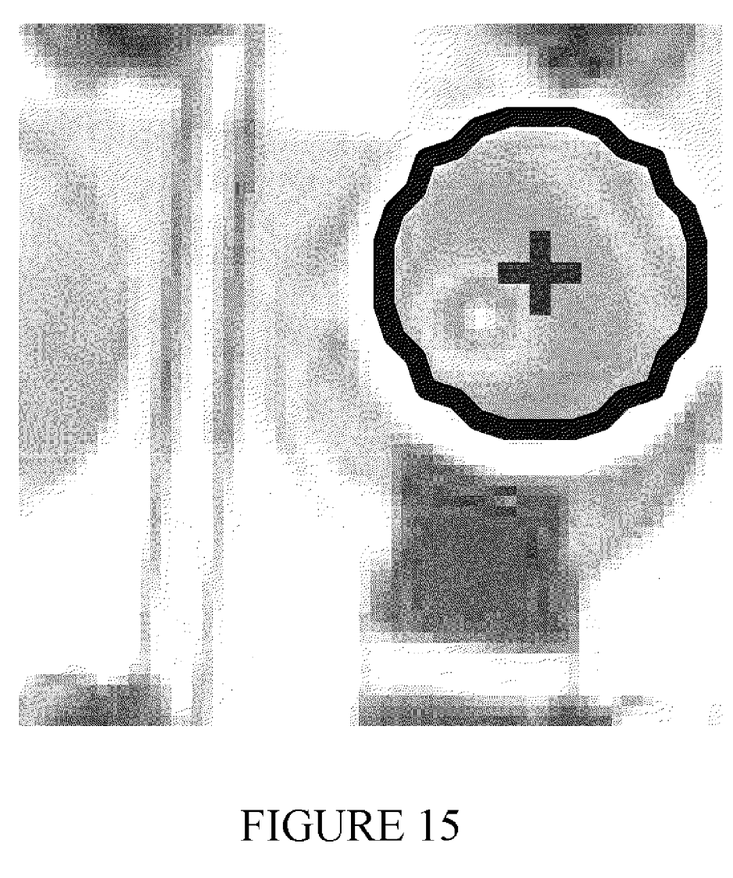
FIG. 15 is a portion of a multiple view image of a test tube that has been processed according to the present invention.

This simplification greatly reduces the computation from all the aspect of the circle Hough transform by using the efficient edge detection and limiting its 3-D parametric estimation space into a very range. The accumulator space and the tube center location result are shown in FIGS. 14 and 15, respectively. This simplified processing may help provide a useful tradeoff between the memory usage, computation complexity, vision processing time, and accuracy.

With respect to barcode decoding, conventional imagers 22 may be equipped with algorithms for decoding symbologies, such as those shown in Table 1. Host 16 may therefore determine which symbologies are enabled and disabled for decoding.

TABLE 1

| Codabar | EAN/JAN-13 | PDF417 |
| Code 39 | EAN/JAN-8 | Micro PDF417 |
| I 2 of 5 | RSS-14 | DataMatrix |
| Code 93 | RSS-Limited | MaxiCode |
| Code 128 | RSS-Expanded | Aztec Code |
| UPC-A | PosiCode | |
| UPC-E0 | Code 49 | |

Barcode symbologies and their decoding algorithms follow the international barcode standards and those of skill in the art will instantly appreciate how to accomplish this functionality through the use of off-the-shelf imagers 14 or decoding packages.

It should be recognized by those of skill in the art that the present invention does not necessarily need to be implemented in a robotic handling system and could be incorporated into any system having the capability to present items for imaging to imager 14 or, alternatively, move imager 14 relative to the target to allow imager 14 to capture images of the target that provide the appropriate field of view containing the aspects of the target that are desired.

What is claimed is:

1. An apparatus for automatically handling an object, comprising:
   a movable arm adapted for grasping and moving said object;
   a mirror positioned on said arm and aligned to provide a reflected image of at least a first portion of said object; and
   an imager positioned to capture a optical image containing at least a second portion of said object and said reflected image of at least said first portion of said object.

2. The apparatus of claim 1, wherein said reflected image comprises a top view of said object and said second portion of said object comprises a side view of said object.

3. The apparatus of claim 2, wherein said imager is aligned along an axis that is non-parallel with respect to the reflected ray axis of the mirror.

4. The apparatus of claim 3, further comprising a rack into and out of which said arm may move said object.

5. The apparatus of claim 4, wherein said imager is associated with a microcontroller that is programmed to process said reflected image to determine the location of the top of said object relative to said arm.

6. The apparatus of claim 5, wherein said microcontroller is programmed to transmit information pertaining to the location of said top of said object based upon said reflected image to said movable arm.

7. The apparatus of claim 6, wherein said imager is aligned along an axis that is non-parallel with respect to the reflected ray axis of the mirror.

8. An apparatus for automatically handling an object, comprising:
   a movable arm adapted for grasping and moving a test tube;
   a mirror positioned on said arm and aligned to provide a reflected view of at least a first portion of said test tube;
   an imager positioned to capture an image of said test tube, wherein said image contains said reflected view of at least said first portion of said test tube and at least a second portion of said test tube; and
   a microcontroller programmed to identify the location of said test tube based on said image.

9. The apparatus of claim 8, wherein said microcontroller is programmed to identify the location of said test tube based on the reflected view of at least a first portion of said test tube.

10. The apparatus of claim 9, wherein said microcontroller is programmed to identify the location of said test tube based on the reflected view of at least a first portion of said test tube by determining the position of a cap positioned on said tube.

11. The apparatus of claim 10, wherein said microcontroller is programmed to determine the position of said cap positioned on said tube by locating the center of said cap.

12. The apparatus of claim 11, wherein said microcontroller is further programmed to decode any encoded information on said test tube that is contained within said image.

13. The apparatus of claim 12, wherein said encoded information is located on the second portion of said test tube.

14. The apparatus of claim 13, wherein said encoded information comprises a barcode.

15. A method of controlling the positioning of a handling apparatus relative to a target object, comprising the steps of:
   positioning a movable arm including a mirror in proximity to said object;
   capturing an image of said object, wherein said image includes a first view of a first portion of said object and a second view of a second portion of said object that has been reflected by said mirror;
   determining the location of the object relative to the movable arm based on the location of said object in said image; and
   aligning said movable arm with said object based on the location of said object relative to said movable arm.

16. The method of claim 15, wherein the step of capturing an image of said object comprises capturing a digital image with an optical imager having a field of view is aligned so that the field of view encompasses at least one side of said object and said mirror at the same time.

17. The method of claim 16, wherein the step of determining the location of the object relative to the movable arm based on the location of said object in said image comprises the steps of identifying the location of the top of said object and calculating the relative position of the movable arm and the object based on the location of the top of said object.

18. The method of claim 16, wherein the step of aligning said movable arm with said object based on the location of said object relative to said robotic arm comprises moving said robotic arm based on the calculated relative position of said top of said object into a position where said robotic arm can grasp said object.

* * * * *